US012575846B2

(12) United States Patent
Nakajima

(10) Patent No.: US 12,575,846 B2
(45) Date of Patent: Mar. 17, 2026

(54) DEVICE WITH VARIABLE RIGIDITY AND SURGICAL GRIPPING DEVICE

(71) Applicant: National University Corporation Tokyo Medical and Dental University, Toyko (JP)

(72) Inventor: Yoshikazu Nakajima, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 755 days.

(21) Appl. No.: 18/012,244

(22) PCT Filed: Jun. 15, 2021

(86) PCT No.: PCT/JP2021/022723
§ 371 (c)(1),
(2) Date: Dec. 22, 2022

(87) PCT Pub. No.: WO2021/261332
PCT Pub. Date: Dec. 30, 2021

(65) Prior Publication Data
US 2023/0130664 A1    Apr. 27, 2023

(30) Foreign Application Priority Data

Jun. 22, 2020    (JP) ................................. 2020-107306

(51) Int. Cl.
A61B 17/29        (2006.01)
A61M 1/00          (2006.01)
A61B 17/00             (2006.01)
(52) U.S. Cl.
CPC ............... A61B 17/29 (2013.01); A61M 1/74 (2021.05); *A61B 2017/00858* (2013.01); *A61B 2017/00862* (2013.01)

(58) Field of Classification Search
CPC .......... A61B 17/29; A61B 2017/00858; A61B 2017/00862; A61B 2017/0225;
(Continued)

(56) References Cited

U.S. PATENT DOCUMENTS 10,434,618 B2 *  10/2019  Corrigan ................ B24D 15/04
2017/0360590 A1  12/2017  Corrigan et al.

FOREIGN PATENT DOCUMENTS

JP        2019-146785        1/2018
JP        2018-500990        9/2019

* cited by examiner

*Primary Examiner* — Joel Lamprecht

(57)        ABSTRACT

In order to provide a device with variable rigidity and a surgical gripping device that make it possible to increase the range of change in rigidity by means of a simple structure, this device with variable rigidity is configured so as to comprise two flexible sheets (12, 14) that include: a base material (20) formed using a sheet-like elastic material and having a plurality of recesses (20B) and a plurality of protrusions (20A) formed on one surface thereof; a low rigidity section (22) that is formed using an elastic material with a lower modulus of elasticity than the base material (20) and that is arranged in the recesses (20B) and joined to the recesses (20B) so that one surface of said low rigidity section (22) becomes flat; and a friction material (24) provided to the one surface. In addition, the two flexible sheets (12, 14) are covered by a bag-like cover with the two pieces of friction material (24) facing each other and are configured so as to have a ventilation port (18) whereby it is possible to suction the air within the flexible sheets (12, 14) and the cover (16) from the exterior of the cover (16).

11 Claims, 7 Drawing Sheets

(58) Field of Classification Search
CPC ........ A61B 2017/2926; A61B 17/0218; A61B
2017/00566; A61B 2017/0212; A61B
2217/005; A61M 1/74; B25J 15/06
See application file for complete search history.

DEVICE WITH VARIABLE RIGIDITY AND SURGICAL GRIPPING DEVICE

RELATED APPLICATIONS

This application is a National Phase of PCT Patent Application No. PCT/JP2021/022723 having International filing date of Jun. 15, 2021, which claims the benefit of priority of Japanese Patent Application No. 2020-107306 filed on Jun. 22, 2020. The contents of the above applications are all incorporated by reference as if fully set forth herein in their entirety.

FIELD AND BACKGROUND OF THE INVENTION

The present disclosure relates to a device with variable rigidity and a surgical gripping device that can be applied to a surgical tool, a robot hand, or the like.

As a surgical instrument, there has been disclosed a structure having a cantilevered first beam formed of a material whose axial rigidity with respect to the longitudinal direction is greater than the bending rigidity, a cantilevered second beam provided so as to be superposed with the first beam and formed of a material whose axial rigidity with respect to the longitudinal direction is greater than the bending rigidity, a film connected to a suction tube and covering the first film and the second film, and one or plural suction portions provided at the first beam (refer to Japanese Patent Application Laid-Open (JP-A) No. 2019-146785). The suction tube is connected to a first pump that sucks a liquid or a gas, and negative pressure is applied thereto by the first pump. The hardnesses of the first beam and the second beam that are covered by the film are adjusted by the magnitude of the negative pressure.

Further, there is disclosed a device that includes locking sheets and whose shape can be formed (refer to Japanese Patent Application National Publication No. 2018-500990). This device has a first state in which the shape of the device can be formed, and a second state in which the device is the desired shape and in which it is substantially more difficult to shape the device than in the first state. The device can further include an envelope that defines a chamber, a port disposed such that fluid can pass between the chamber and the periphery, and at least two locking sheets disposed within the chamber and structured so as to at least partially overlap. By being joined together, the two locking sheets can substantially form a single, rigid sheet.

SUMMARY OF THE INVENTION

For example, in laparoscopic surgery, at the time of separating an organ such as the liver or the like by scissors, in order to efficiently separate the organ, there are cases in which the periphery of the portion that is to be separated is gripped by a gripping instrument. Currently, gripping instruments that are formed of a material of high rigidity such as stainless steel or the like or a material of low rigidity such as rubber or the like are mainly used. If the gripping instrument is a gripping instrument of a material that has high rigidity such as scissors-like forceps or the like, the gripped surface area is small, and there also is the concern that the organ will be affected. Further, if the gripping instrument is a gripping instrument of a material that has low rigidity, the organ can be gripped in a shape that follows along the organ, and the gripped surface area can be made to be large, but, because the rigidity is low, there is the possibility that, in the gripped state, the organ will move, and it will not be possible to separate the organ efficiently with scissors.

On the other hand, devices based on the "jamming transition phenomenon" in which a fine powder is filled into a bag-shaped container formed of a soft material and the air in the interior is sucked so as to increase the rigidity, focus attention on the field of soft robotics. However, there is the shortcoming that, because the filler is a powder, strength with respect to load in the direction of stripping-off the powder is not retained.

When considering the background art from the standpoint of practical application, almost all devices that grip soft tissue or an organ surface by adsorption are devices whose rigidity is not varied, and a gripping instrument whose rigidity is varied does not exist except for the background art disclosed in aforementioned Patent Document 1. In Patent Document 1 as well, optimization of materials and structures is not mentioned at all, and Patent Document 1 merely describes the basic theory and the basic structure for bringing about a change in rigidity.

An object of the present disclosure is to provide a device with variable rigidity and a surgical gripping device that, by a simple structure, can increase the range of variation in rigidity.

A device with variable rigidity relating to a first aspect comprises two flexible sheets having: a base material structured by a sheet-shaped elastic material, one surface of which has a plurality of recesses and a plurality of protrusions; a low rigidity portion disposed at the recesses and joined to the recesses such that the one surface is flat, and structured by an elastic material of a lower modulus of elasticity than the base material; and a friction material provided at the one surface, wherein the two flexible sheets are covered by a bag-shaped cover in a state in which the friction materials face one another, wherein and the device with variable rigidity further has a vent hole that enables suction of a fluid, which is between the flexible sheets and within the cover, from an exterior of the cover.

In this device with variable rigidity, the two flexible sheets are covered by the bag-shaped cover in a state in which the friction materials face one another. Before the fluid that is between the flexible sheets and within the cover is sucked from the exterior of the cover, i.e., in a state in which the interior of the cover is atmospheric pressure, the two flexible sheets do not adhere to one another, and the two flexible sheets respectively are deformable. Further, in the state in which the two flexible sheets do not adhere to one another, the frictional force generated between the friction materials is low, and therefore, it is difficult for the deformations of the two flexible sheets 12, 14 to hinder one another. Accordingly, the shapes of the flexible sheets can be varied such that the device with variable rigidity runs along a gripped object.

When the fluid, which is between the flexible sheets and within the cover, is sucked from the exterior of the cover through the vent hole, the two flexible sheets adhere, and a type of jamming transition phenomenon occurs, and the flexible sheets are made integral. At this time, because the friction materials adhere to one another, it is difficult for the two flexible sheets to slide with respect to one another, and relative deformation of the two flexible sheets is suppressed. By making the two flexible sheets integral in this way, the bending rigidity is higher than in a case in which there is a single flexible sheet. Because the jamming transition phenomenon is utilized, heat is not generated, and moreover, the bending rigidity can be varied immediately, which is different than in a case utilizing a chemical reaction.

Moreover, the flexible sheets have the base materials, and the low rigidity portions that are structured by an elastic material of a lower modulus of elasticity than the base materials. Therefore, the bending rigidities of the flexible sheets in the state in which the interior of the cover is atmospheric pressure are low, as compared with a case in which the flexible sheets are structured only by the base materials, and the low rigidity portions are not provided. Therefore, the range of varying the rigidity can be enlarged by a simple structure.

In a second aspect, in the device with variable rigidity relating to the first aspect, due to reinforcing materials that extend in a predetermined direction, extension/contraction of the base materials in the predetermined direction is suppressed, and the base materials can deform by bending.

In this device with variable rigidity, due to the reinforcing materials that extend in a predetermined direction, extension/contraction of the base materials of the flexible sheets in the predetermined direction is suppressed. Therefore, the flexible sheets contracting in the predetermined direction at the time of suction of the fluid within the cover, and the shapes of the flexible sheets changing further from shapes of running along the gripped object, are suppressed.

In a third aspect, in the device with variable rigidity relating to the first aspect or the second aspect, in the friction material of one of the flexible sheets has a groove that communicates with the vent hole without contacting another of the flexible sheets at a time of suction of fluid that is between the flexible sheets.

In this device with variable rigidity, in the friction material of one of the flexible sheets has the groove that communicates with the vent hole without contacting the another of the flexible sheets at the time of suction of the fluid that is between the flexible sheets. Therefore, even though the flexible sheets adhere to one another at the time of suction, a flow path of fluid that communicates with the vent hole remains. Accordingly, as compared with a case in which the groove does not exist, it is easy for the fluid to slip out from between the flexible sheets, and the fluid that remains between the flexible sheets can be reduced. Further, due thereto, the adhesion of the two flexible sheets to one another can be increased.

In a fourth aspect, in the device with variable rigidity relating to any one of the first through third aspects, a through-hole that passes through in a thickness direction is formed in one of the flexible sheets, and an adsorbing member, which is air permeable overall and which can adsorb a gripped object, is provided at a surface, which is at a side opposite from the friction material, of the one of the flexible sheets.

In this device with variable rigidity, the through-hole that passes through in the thickness direction is formed in one of the flexible sheets. The adsorbing member, which is air permeable overall and which can adsorb a gripped object, is provided at the surface, which is at the side opposite from the friction material, of that flexible sheet. Therefore, the device with variable rigidity can be made to adsorb a gripped object.

In a fifth aspect, in the device with variable rigidity relating to a fourth aspect, the cover covers the entire device other than the adsorbing member, so as to prevent flowing-in of air from an exterior of the device at a time of adsorption and so as to maintain negative pressure within the device due to suction at a time of adsorption.

In a sixth aspect, in the device with variable rigidity relating to any one of the first through fifth aspects, a handle for manipulation is provided at the flexible sheet.

In this device with variable rigidity, by grabbing the handle by an instrument such as forceps or the like, the gripped object that is gripped by the device with variable rigidity can be manipulated freely.

A surgical gripping device relating to a seventh aspect comprises two flexible sheets each having: a base material structured by a sheet-shaped elastic material, one surface of which has a plurality of recesses and a plurality of protrusions; a low rigidity portion disposed at the recesses and joined to the recesses such that the one surface is flat, and structured by an elastic material of a lower modulus of elasticity than the base material; and a friction material provided at the one surface, wherein the two flexible sheets are covered by a bag-shaped cover in a state in which the friction materials face one another, wherein the surgical gripping device further has a vent hole that enables suction of a fluid, which is between the flexible sheets and within the cover, from an exterior of the cover, wherein a through-hole that passes through in a thickness direction is formed in one of the flexible sheets, wherein an adsorbing member, which is air permeable overall and which can adsorb a gripped object, is provided at a surface, which is at a side opposite from the friction material, of the one of the flexible sheets, and wherein the surgical gripping device can cause the adsorbing member to adsorb an organ, and can grip the organ.

In an eighth aspect, in the surgical gripping device relating to the seventh aspect, due to reinforcing materials that extend in a predetermined direction, extension/contraction of the base materials in the predetermined direction is suppressed, and the base materials can deform by bending.

In a ninth aspect, in the surgical gripping device relating to the seventh aspect or the eighth aspect, in the friction material of one of the flexible sheets has a groove that communicates with the vent hole without contacting another of the flexible sheets at a time of suction of fluid that is between the flexible sheets.

In a tenth aspect, in the surgical gripping device relating to any one of the seventh through ninth aspects, the cover covers the entire device other than the adsorbing member, so as to prevent flowing-in of air from an exterior of the device at a time of adsorption and so as to maintain negative pressure within the device due to suction at a time of adsorption.

In an eleventh aspect, in the surgical gripping device relating to any one of the seventh through tenth aspects, a handle for manipulation is provided at one of the flexible sheets.

In accordance with the present disclosure, there can be provided a device with variable rigidity and a surgical gripping device that, by a simple structure, can increase the range of varying the rigidity.

DESCRIPTION OF SPECIFIC EMBODIMENTS OF THE INVENTION

Figure 1:
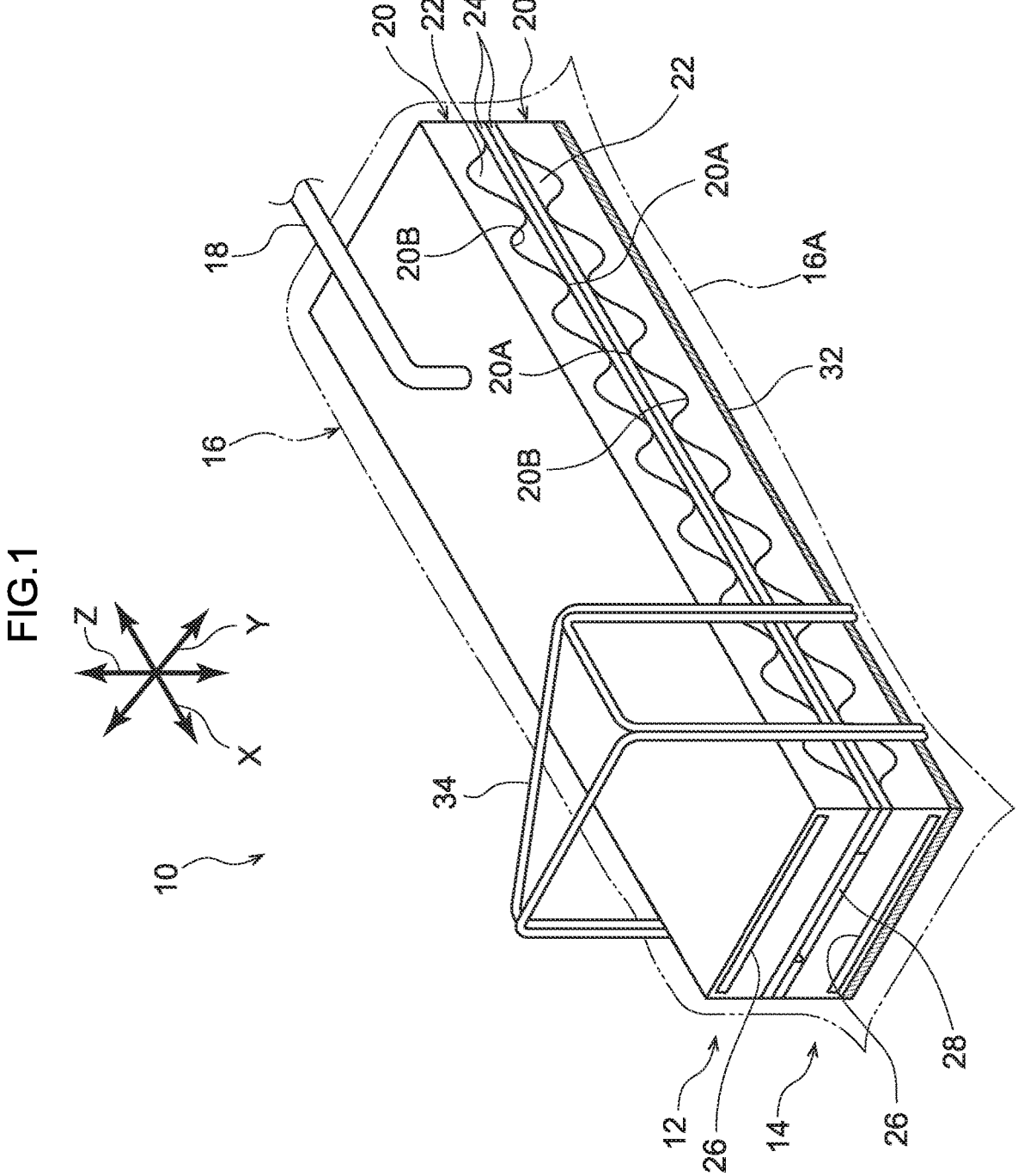
FIG. 1 is a perspective view illustrating a surgical gripping device relating to an embodiment of the present disclosure.

An embodiment of the present disclosure is described hereinafter on the basis of the drawings. Structural elements that are illustrated by using the same reference numerals in the respective drawings mean the same structural elements. Note that, in the embodiment described hereinafter, there are cases in which repeat description and reference numerals are omitted.

In the drawings, the arrow X direction indicates the longitudinal direction of a surgical gripping device, the arrow Y direction indicates the width direction of the surgical gripping device, and the arrow Z direction indicates the height direction of the surgical gripping device. In the present embodiment, "rigidity" means bending rigidity.

In FIG. 1, a surgical gripping device 10 relating to the present embodiment is a type of a device with variable rigidity, and has two flexible sheets 12, 14, a cover 16, and a vent hole 18. The two flexible sheets 12, 14 are, in a state in which friction materials 24 that are described hereafter face one another, covered by the bag-shaped cover 16.

Each of the flexible sheets 12, 14 has a base material 20, a low rigidity portion 22 and the friction material 24. The base material 20 is structured by an elastic material, e.g., rubber, that is shaped as a sheet. The planar shapes of the base material 20 are rectangular for example, but may be another shape such as another quadrangular shape, a polygonal shape other than quadrangular, circular, elliptical, oval or the like. Due to a reinforcing material 26 that extends in a predetermined direction, extension/contraction of the base material 20 in the predetermined direction is suppressed, and the base material 20 can deform by bending. The predetermined direction is, for example, the longitudinal direction shown by arrow X in the drawings. For example, a belt using aromatic polyamide fibers is used as the reinforcing material 26. Note that the reinforcing materials 26 are illustrated only in FIG. 1, and illustration thereof is omitted in the other drawings.

Plural recesses 20B and plural protrusions 20A are formed at one surface of the base material 20. Specifically, in consideration of the ease of machining, the recesses 20B and the protrusions 20A respectively extend in the width direction (the Y direction), and are formed rectilinearly over the entire width of the base material 20. Further, the recesses 20B and the protrusions 20A are disposed alternately in the longitudinal direction (the arrow X direction). In a front view seen from the arrow Y direction, the recesses 20B and the protrusions 20A are formed continuously in a sine wave shape.

The low rigidity portion 22 is filled and disposed at the recesses 20B and is joined to the recesses 20B such that one surface of the base material 20 is flat. The low rigidity portion 22 is structured by using an elastic material of a lower modulus of elasticity than the base material 20. For example, a caulking material such as silicon or urethane can be used as this elastic material. In this way, the flexible sheets 12, 14 are three-layer structures of the base material 20 that has relatively high rigidity, the low rigidity portion

22 that has relatively low rigidity, and the friction material 24. Using the flexible sheet 12 as an example, in the base material 20, the upper layer that does not have the recesses 20B and protrusions 20A, has the highest rigidity. At the lower layer that is structured by the protrusions 20A and the recesses 20B that have the low rigidity portion 22, portions of high rigidity and portions of low rigidity exist alternately in the longitudinal direction, and this lower layer has low rigidity as compared with the upper layer, and has high rigidity as compared with only the low rigidity portion 22.

Figure 4:
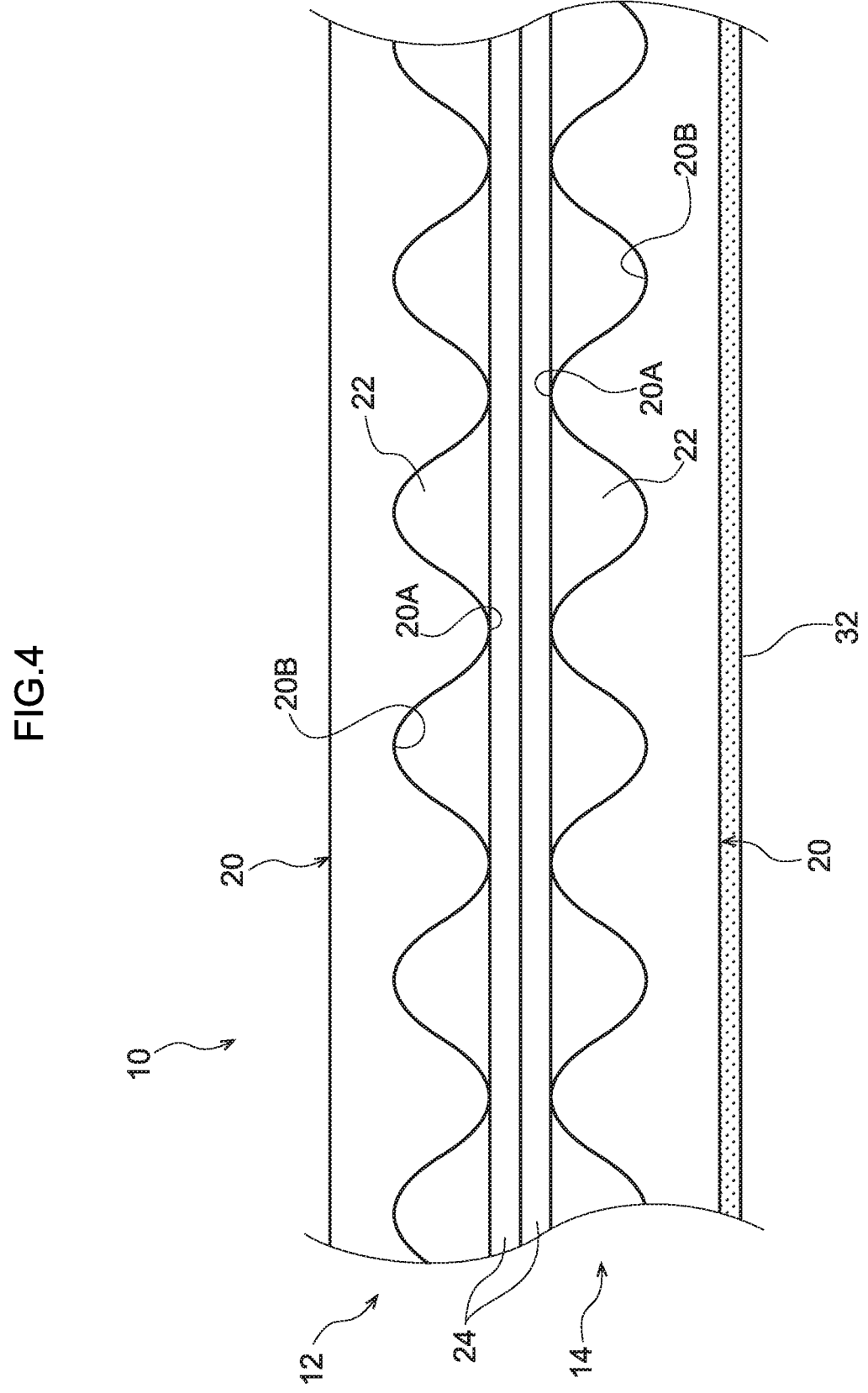
FIG. 4 is a front view illustrating the surgical gripping device relating to the embodiment in an enlarged manner.

The friction material 24 is provided on one surface of the base material 20, and, for example, is structured from an elastic material such as rubber or the like that has a greater coefficient of friction than the base material 20 and the low rigidity portion 22. The coefficient of friction is set such that, at the time of suction of the interior of the cover 16, relative sliding between the two flexible sheets 12, 14 can be suppressed. Further, from the standpoint of ensuring the bending rigidity of the surgical gripping device 10, it is preferable that the peak portions of the protrusions 20A of the base material 20 contact the friction material 24, but the low rigidity portion 22 may be slightly interposed between these peak portions and the friction material 24. As illustrated in FIG. 4, the peak portions of the protrusions 20A of the base materials 20 at the flexible sheets 12, 14 are disposed so as to face one another in the vertical direction (the arrow Z direction).

Figure 2:
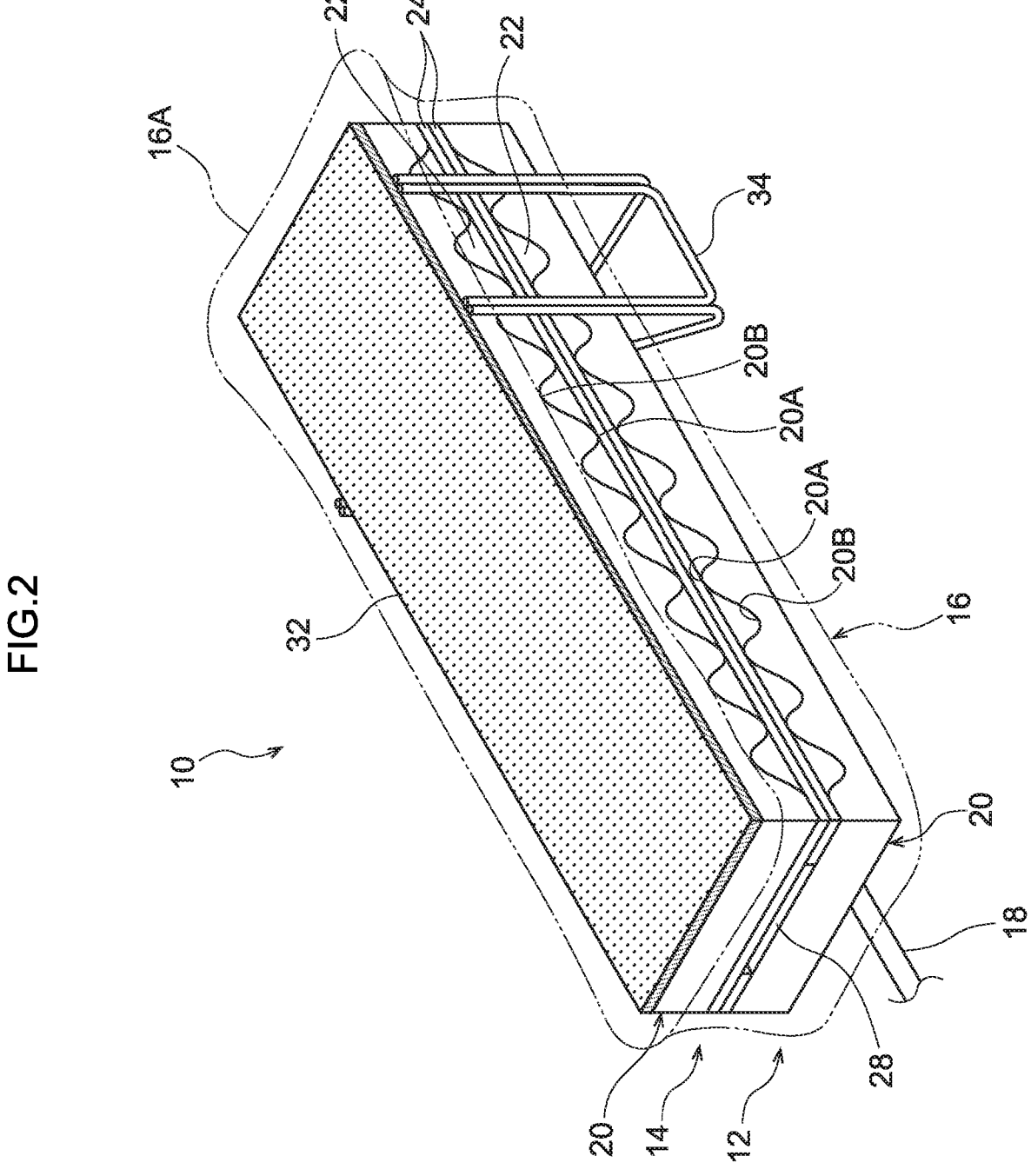
FIG. 2 is a perspective view illustrating a state in which the surgical gripping device relating to the embodiment of the present disclosure is seen from a bottom surface side.
Figure 3:
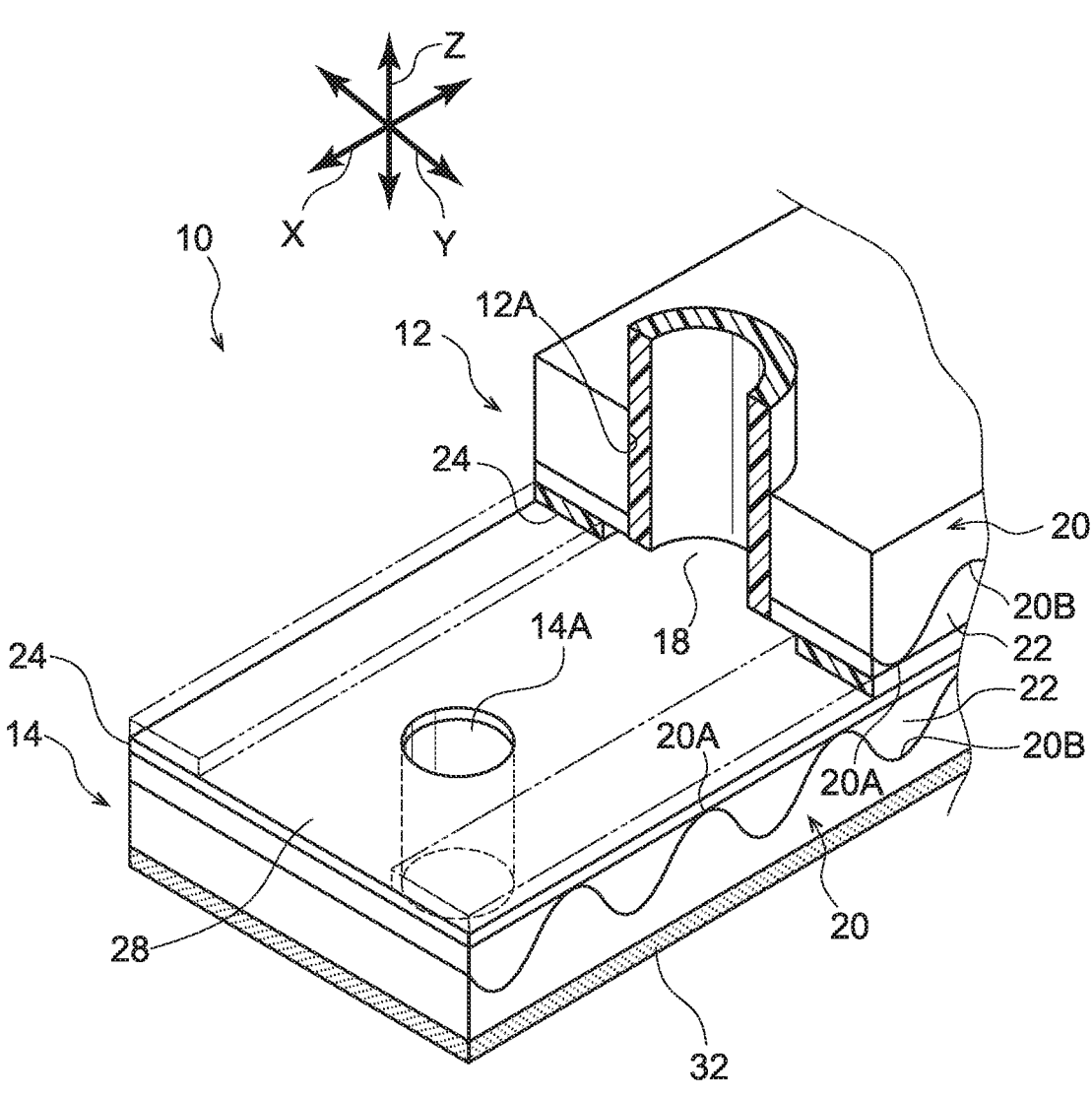
FIG. 3 is a partially broken perspective view illustrating the surgical gripping device relating to the embodiment.

As illustrated in FIG. 1 through FIG. 3, in the friction material 24 of one of the flexible sheets, e.g., the flexible sheet 12 at the upper side has a groove 28 that communicates with the vent hole 18 without contacting the other flexible sheet, i.e., the flexible sheet 14 at the lower side, at the time of suction of air that is an example of the fluid between the flexible sheets 12, 14. The groove 28 is structured, for example, by omitting the friction material 24 over the entire length in the longitudinal direction (the arrow X direction) at the central portion in the width direction (the arrow Y direction) of the flexible sheet 12. In other words, the bottom surface of the flexible sheet 12 that is at the upper side is exposed at the portion of the groove 28. Note that the groove 28 may be structured by a portion of the friction material 24 being formed to be thin-walled. Or, plural guiding grooves (not illustrated) that communicate with the groove 28 may be provided at the friction material 24. In this case, pockets of accumulated air between the friction materials 24 that face one another can be decreased further. Further, the groove may be provided at the friction material 24 of the flexible sheet 14 that is at the lower side.

The vent hole 18 is a pipe that enables suction of the air, which is between the flexible sheets 12, 14 and within the cover 16, from the exterior of the cover 16, and, for example, is provided so as to pass-through the cover 16. As illustrated in FIG. 3, in the present embodiment, the vent hole 18 passes-through the cover 16, and further passes through the flexible sheet 12 at the upper side, and opens at the groove 28. Note that the vent hole 18 may be structured so as to open at a through-hole 12A provided in the flexible sheet 12 that is at the upper side. Further, in the case of a structure in which the surgical gripping device 10 does not adsorb a gripped object 30 (FIG. 6, FIG. 7), there may be a structure in which the vent hole 18 opens at the interior of the cover 16 and does not pass-through the flexible sheet 12.

Figure 5:
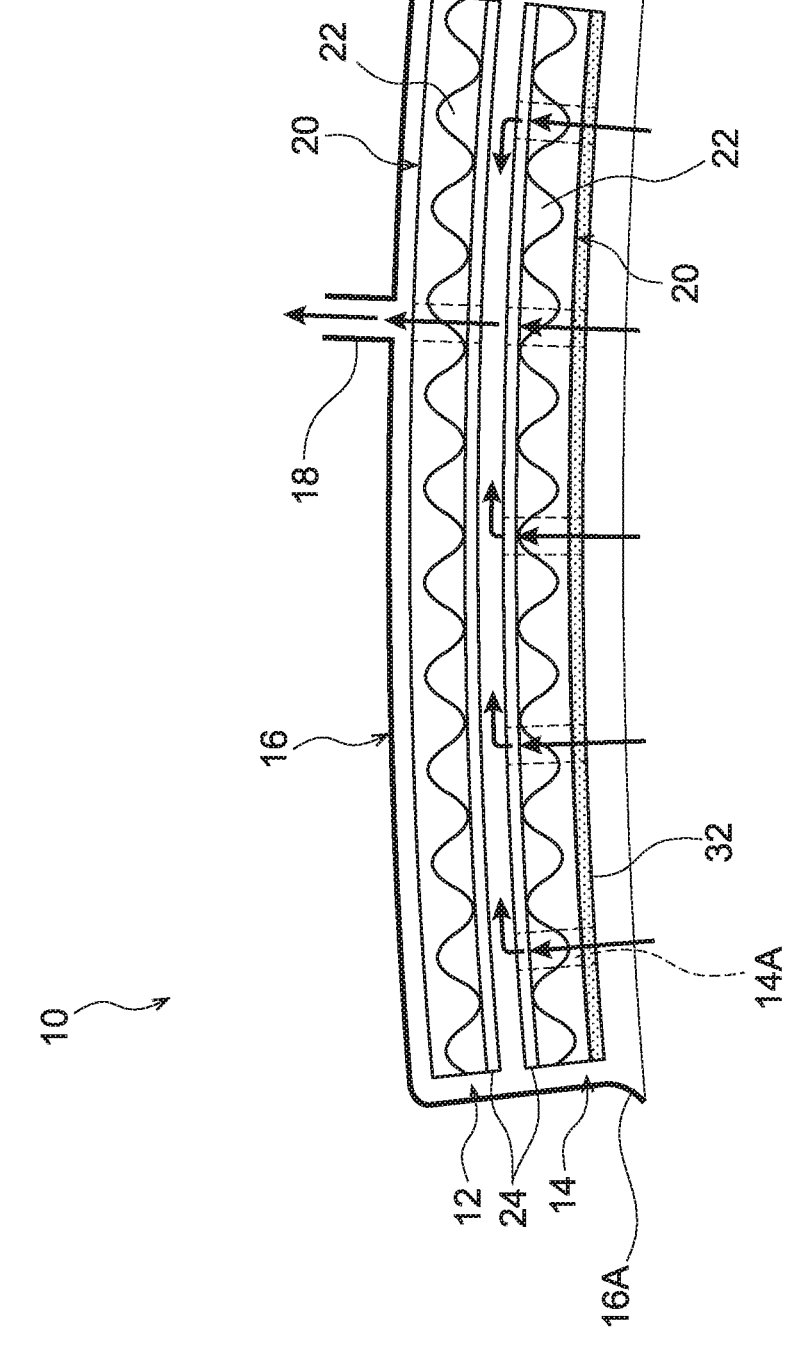
FIG. 5 is a front view illustrating the flow of air within a cover and between flexible sheets at a time of sucking air from a vent hole.
Figure 6:
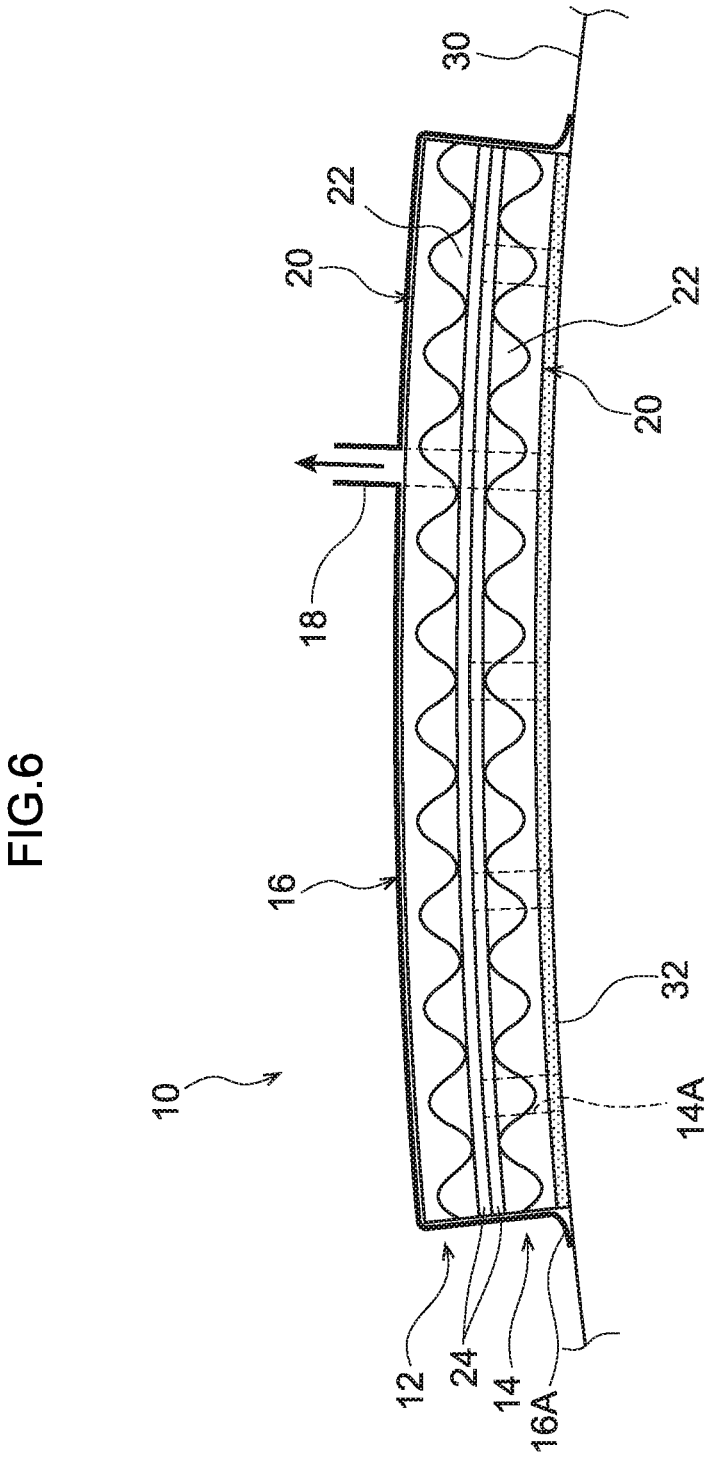
FIG. 6 is a front view illustrating a state in which the surgical gripping device has adsorbed a gripped object.

Through-holes 14A that pass through in the thickness direction are formed in one of the flexible sheets, e.g., the flexible sheet 14 at the lower side. The plural through-holes 14A are provided along the longitudinal direction (the arrow X direction), and respectively open at the groove 28 (FIG. 5, FIG. 6). An adsorbing member 32, which is air permeable overall and can adsorb the gripped object 30, may be provided at the surface at the side opposite from the friction material 24, i.e., a bottom surface 14B, of the flexible sheet 14. The adsorbing member 32 is structured of a material that is air permeable and flexible, such as a sponge or the like for example.

As illustrated in FIG. 1 and FIG. 2, a handle 34 for manipulation may be provided, for example, at the flexible sheet 14 that is at the lower side. This handle 34 has three leg portions 34B, and a triangular ring 34A that connects the upper ends of the leg portions 34B in a triangular shape. The handle 34 is a structure in which, for example, among three wires that are substantially U-shaped, the portions that structure the leg portions 34B of the handle 34 are set close to one another or are made to abut one another, and are fixed to side surfaces of the flexible sheet 14. Due thereto, due to one side of the triangular ring 34A and one place of the leg portions 34B of the handle 34 being gripped at one time by a gripping instrument such as forceps 36 (FIG. 7) or the like, application of torque to the surgical gripping device 10 also is easy, and the ability to manipulate is good.

The bag-shaped cover 16 has a volume that is slightly larger than the volumes of the two flexible sheets 12, 14 and the adsorbing member 32, and accommodates these flexible sheets 12, 14 and adsorbing member 32. A membrane 16A that extends in the longitudinal direction and the width direction of the flexible sheet 14 is provided at the lower edge of the cover 16, at the periphery of the adsorbing member 32. The membrane 16A adheres to the periphery of the adsorbing member 32. Note that the cover 16 may be transparent or may be opaque.

Operation

Figure 7:
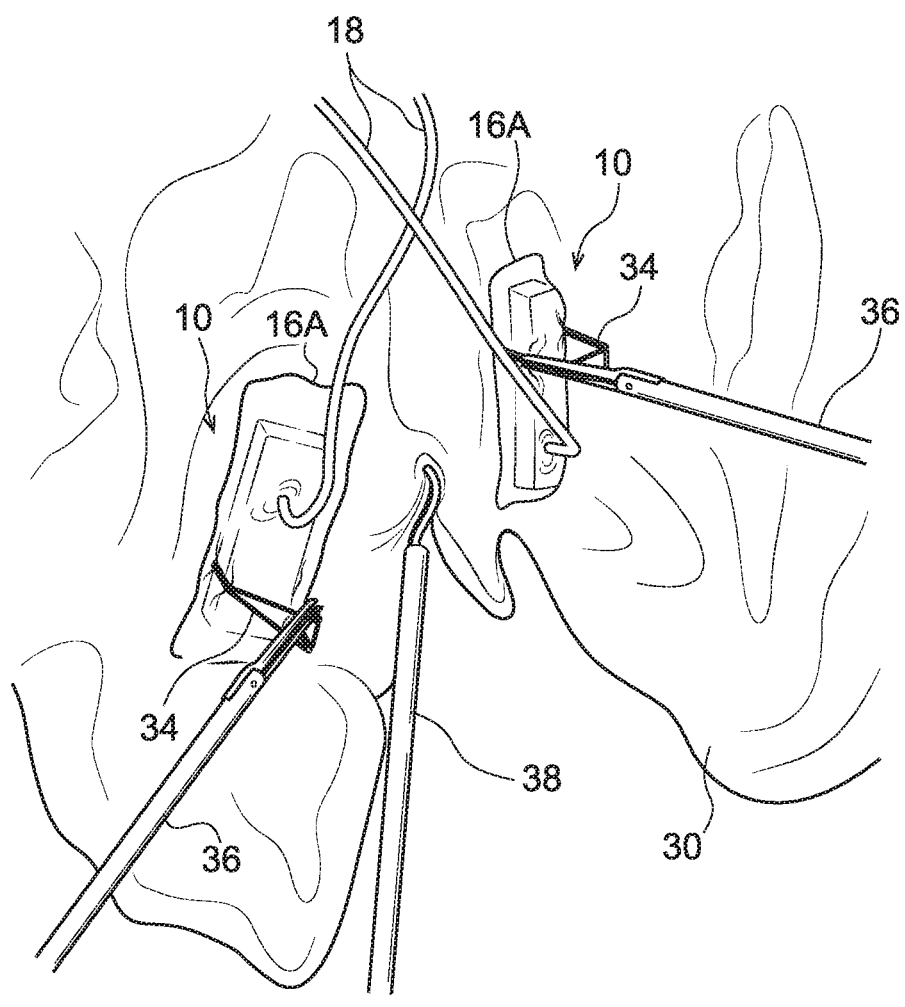
FIG. 7 is a perspective view illustrating a state of usage of the surgical gripping device.

The present embodiment is structured as described above, and operation thereof is described hereinafter. In FIG. 5, at the surgical gripping device 10 relating to the present embodiment, the two flexible sheets 12, 14 are covered by the bag-shaped cover 16 in a state in which the friction materials 24 face one another. Before the air, which is between the flexible sheets 12, 14 and within the cover 16, is sucked from the exterior of the cover 16, i.e., in a state in which the interior of the cover 16 is atmospheric pressure, the two flexible sheets 12, 14 do not adhere to one another, and the two flexible sheets 12, 14 are respectively deformable. Further, in the state in which the two flexible sheets 12, 14 do not adhere to one another, the frictional force generated between the friction materials 24 is low, and therefore, it is difficult for the deformations of the two flexible sheets 12, 14 to hinder one another. Accordingly, the shapes of the flexible sheets 12, 14 can be varied such that the surgical gripping device runs along the gripped object 30 (FIG. 6, FIG. 7).

Next, in FIG. 6, when the air, which is between the flexible sheets 12, 14 and within the cover 16, is sucked from the exterior of the cover 16 through the vent hole 18, the two flexible sheets 12, 14 adhere, and a type of jamming transition phenomenon occurs, and the flexible sheets 12, 14 are made integral. In the present embodiment, formed in the friction material 24 of one of the flexible sheets 12, 14 is the groove 28 that communicates with the vent hole 18 without contacting the other flexible sheet 12, 14 at the time when the air between the flexible sheets 12, 14 is sucked. Therefore, even though the flexible sheets 12, 14 adhere to one another at the time of suction, a flow path of air that communicates with the vent hole 18 remains. Accordingly, as compared with a case in which the groove 28 does not exist, it is easy for air to slip out from between the flexible sheets 12, 14, and the air that remains between the flexible sheets 12, 14 can be reduced. Further, due thereto, the adhesion of the two flexible sheets 12, 14 to one another can be increased.

Because the friction materials 24 adhere to one another, it is difficult for the two flexible sheets 12, 14 to slide with respect to one another, and relative deformation of the two flexible sheets 12, 14 is suppressed. By making the two flexible sheets 12, 14 integral in this way, the bending rigidity is higher than in a case in which there is the single flexible sheet 12, 14. Because the jamming transition phenomenon is utilized, heat is not generated, and moreover, the bending rigidity can be varied immediately, which is different than in a case utilizing a chemical reaction. Because extension/contraction of the base materials 20 of the flexible sheets 12, 14 in the longitudinal direction is suppressed by the reinforcing materials 26, the flexible sheets 12, 14 contracting in the longitudinal direction at the time when the air within the cover 16 is sucked, and the shapes of the flexible sheets 12, 14 changing further from shapes of running along the gripped object 30, are suppressed.

Moreover, the flexible sheets 12, 14 have the base materials 20, and the low rigidity portions 22 that are structured by using an elastic material of a lower modulus of elasticity than the base materials 20. Therefore, the bending rigidities of the flexible sheets 12, 14 in the state in which the interior of the cover 16 is atmospheric pressure are low, as compared with a case in which the flexible sheets 12, 14 are structured only by the base materials 20, and the low rigidity portions 22 are not provided thereat. Therefore, the range of varying the rigidity can be enlarged by a simple structure.

In the present embodiment, the through-holes 14A that pass through in the thickness direction are formed in one of the flexible sheets 12, 14, and the adsorbing member 32, which is air permeable overall and which can adsorb the gripped object, is provided at the surface of that flexible sheet 12, 14, which surface is at the side opposite from the friction material 24. Accordingly, the surgical gripping device 10 can be made to adsorb the gripped object 30. Because the membrane 16A is provided at the periphery of the adsorbing member 32, the force of adsorbing the gripped object 30 can be increased.

Simultaneously with the surgical gripping device 10 adsorbing, for example, an organ that is the gripped object 30, the vent hole 18 is closed, and the surgical gripping device 10 transitions to a highly rigid state.

Moreover, in FIG. 7, by grabbing the handle 34 by an instrument such as the forceps 36 or the like, the gripped object 30 that is adsorbed by the surgical gripping device 10 can be manipulated freely. Because the bending rigidity of the flexible sheets 12, 14 increases due to the adsorbing, the manipulating force applied to the surgical gripping device 10 from an instrument such as the forceps 36 or the like is efficiently transmitted to the gripped object 30. Due thereto, at the time of surgery when a portion of the organ that serves as an example of the gripped object 30 is separated by scissors 38, for example, two of the surgical gripping devices 10 are made to adsorb the organ, and the work of imparting forces in two directions to the organ is easy.

Further, because the adsorbing member 32 is air permeable overall, local adsorbing of the gripped object 30 is suppressed, and effects on the gripped object 30 due to adsorption can be suppressed. In accordance with the present disclosure, there can be provided an improved device with variable rigidity and surgical gripping device 10.

Other Embodiments

Although an example of an embodiment of the present disclosure has been described above, embodiments of the present disclosure are not limited to the above, and the present disclosure can, of course, be implemented by being modified in various ways other than the above within a scope that does not depart from the gist thereof.

In the above-described embodiment, the groove 28 is formed in the friction material 24, but the groove 28 may be omitted. Further, although there is a structure in which the surgical gripping device 10 adsorbs the gripped object 30, there may be a structure in which the gripped object 30 is not adsorbed. Specifically, there may be a structure in which the through-holes 14A are not provided in the flexible sheet 14 that is at the lower side, and further, the adsorbing member 32 is not provided. A case in which the surgical gripping device 10 is set at the finger of a robot arm can be contemplated as an example thereof (not illustrated). Because the gripped object can be gripped by the gripping force of the robot arm, the surgical gripping device 10 does not have to adsorb the gripped object.

Although the handle 34 for manipulation is provided at the flexible sheet 14, the handle 34 does not have to be provided, provided that there is means by which the surgical gripping device 10 can be manipulated.

Although air is given as an example of the fluid, the fluid may be a gas other than air or a liquid.

The disclosure of Japanese Patent Application No. 2020-107306 filed on Jun. 22, 2020 is, in its entirety, incorporated by reference into the present specification.

All publications, patent applications, and technical standards mentioned in the present specification are incorporated by reference into the present specification to the same extent as if such individual publication, patent application, or technical standard was specifically and individually indicated to be incorporated by reference.

What is claimed is:

1. A device with variable rigidity, the device comprising two flexible sheets each having:
   a base material structured by a sheet-shaped elastic material, one surface of which has a plurality of recesses and a plurality of protrusions;
   a low rigidity portion disposed at the recesses and joined to the recesses such that the one surface is flat, and structured by an elastic material of a lower modulus of elasticity than the base material; and
   a friction material provided at the one surface,
   wherein the two flexible sheets are covered by a bag-shaped cover in a state in which the friction materials face one another, and
   wherein the device with variable rigidity further has a vent hole that enables suction of a fluid, which is between the flexible sheets and within the cover, from an exterior of the cover.

2. The device with variable rigidity of claim 1, wherein, due to reinforcing materials that extend in a predetermined direction, extension/contraction of the base materials in the predetermined direction is suppressed, and the base materials can deform by bending.

3. The device with variable rigidity of claim 1, wherein the friction material of one of the flexible sheets has a groove that communicates with the vent hole without contacting another of the flexible sheets at a time of suction of fluid that is between the flexible sheets.

4. The device with variable rigidity of claim 1, wherein:
   a through-hole that passes through in a thickness direction is formed in one of the flexible sheets, and
   an adsorbing member, which is air permeable overall and which can adsorb a gripped object, is provided at a surface, which is at a side opposite from the friction material, of the one of the flexible sheets.

5. The device with variable rigidity of claim 4, wherein the cover covers the entire device other than the adsorbing member, so as to prevent flowing-in of air from an exterior of the device at a time of adsorption and so as to maintain negative pressure within the device due to suction at a time of adsorption.

6. The device with variable rigidity of claim 1, wherein a handle for manipulation is provided at the flexible sheet.

7. A surgical gripping device comprising two flexible sheets each having:
   a base material structured by a sheet-shaped elastic material, one surface of which has a plurality of recesses and a plurality of protrusions;
   a low rigidity portion disposed at the recesses and joined to the recesses such that the one surface is flat, and structured by an elastic material of a lower modulus of elasticity than the base material; and
   a friction material provided at the one surface,
   wherein the two flexible sheets are covered by a bag-shaped cover in a state in which the friction materials face one another,
   wherein the surgical gripping device further has a vent hole that enables suction of a fluid, which is between the flexible sheets and within the cover, from an exterior of the cover,
   wherein a through-hole that passes through in a thickness direction is formed in one of the flexible sheets,
   wherein an adsorbing member, which is air permeable overall and which can adsorb a gripped object, is provided at a surface, which is at a side opposite from the friction material, of the one of the flexible sheets, and
   wherein the surgical gripping device can cause the adsorbing member to adsorb an organ, and can grip the organ.

8. The surgical gripping device of claim 7, wherein, due to reinforcing materials that extend in a predetermined direction, extension/contraction of the base materials in the predetermined direction is suppressed, and the base materials can deform by bending.

9. The surgical gripping device of claim 7, wherein the friction material of one of the flexible sheets has a groove that communicates with the vent hole without contacting another of the flexible sheets at a time of suction of fluid that is between the flexible sheets.

10. The surgical gripping device of claim 7, wherein the cover covers the entire device other than the adsorbing member, so as to prevent flowing-in of air from an exterior of the device at a time of adsorption and so as to maintain negative pressure within the device due to suction at a time of adsorption.

11. The surgical gripping device of claim 7, wherein a handle for manipulation is provided at one of the flexible sheets.

* * * * *